United States Patent
Bischoff et al.

(10) Patent No.: US 8,502,113 B2
(45) Date of Patent: *Aug. 6, 2013

(54) APPARATUS AND METHOD FOR MATERIAL PROCESSING USING A TRANSPARENT CONTACT ELEMENT

(75) Inventors: Mark Bischoff, Jena (DE); Gregor Stobrawa, Jena (DE)

(73) Assignee: Carl Zeiss Meditec AG, Jena (DE)

(*) Notice: Subject to any disclaimer, the term of this patent is extended or adjusted under 35 U.S.C. 154(b) by 193 days.

This patent is subject to a terminal disclaimer.

(21) Appl. No.: 12/983,743

(22) Filed: Jan. 3, 2011

(65) Prior Publication Data
US 2011/0102810 A1    May 5, 2011

Related U.S. Application Data

(62) Division of application No. 11/864,500, filed on Sep. 28, 2007, now Pat. No. 7,863,543.

(30) Foreign Application Priority Data

Sep. 29, 2006 (DE) .......................... 10 2006 046 370

(51) Int. Cl.
*B23K 26/00* (2006.01)
*A61B 18/20* (2006.01)

(52) U.S. Cl.
USPC .......................................... 219/121.72; 606/5

(58) Field of Classification Search
USPC .............. 219/121.6–121.86; 356/123–125, 356/496, 511, 512; 361/205–212; 606/3–5, 606/10–12
See application file for complete search history.

(56) References Cited

U.S. PATENT DOCUMENTS

| 4,856,513 A | 8/1989 | Muller |
| 4,941,093 A | 7/1990 | Marshall et al. |
| 5,549,632 A | 8/1996 | Lai |
| 6,086,204 A | 7/2000 | Magnante |

(Continued)

FOREIGN PATENT DOCUMENTS

| DE | 198 31 674 A1 | 1/2000 |
| DE | 103 54 025 A1 | 6/2005 |

(Continued)

OTHER PUBLICATIONS

Drexler, W., et al., "Submicrometer Precision Biometry of the Anterior Segment of the Human Eye," *Investigative Ophthalmology & Visual Science*, vol. 38, No. 7, pp. 1304-1313 (1997).
*Intralase Product Leaflet*, Essential Technology for Biomechanical Stability, Intralase Corp., 6 pgs. (2006).

*Primary Examiner* — Sang Paik
(74) *Attorney, Agent, or Firm* — Douglas J. Christensen

(57) ABSTRACT

A method of preparing an apparatus for material processing by generating optical breakthroughs in an object. The apparatus includes a variable focus adjustment device. A contact element is mounted to the apparatus, the contact element has a curved contact surface having a previously known shape. The position of the contact surface is determined prior to processing the object, by focusing measurement laser radiation near or on the surface by the variable focus adjustment device, and the focus position is adjusted in a measurement surface intersecting the expected position of the contact surface. Radiation from the focus of the measurement laser radiation is confocally detected. The position of points of intersection between the measurement surface and the contact surface is determined from the confocally detected radiation to determine the position of the contact surface from the position of the points of intersection and the previously known shape of the contact surface.

21 Claims, 2 Drawing Sheets

(56) References Cited

U.S. PATENT DOCUMENTS

| | | |
|---|---|---|
| 6,373,571 B1 | 4/2002 | Juhasz et al. |
| 6,713,718 B1 | 3/2004 | Lu |
| 6,786,602 B2 | 9/2004 | Abitbol |
| 7,330,275 B2 | 2/2008 | Raksi |
| 7,402,159 B2 | 7/2008 | Loesel |
| 7,440,115 B2 | 10/2008 | Horwitz |
| 7,692,865 B2 | 4/2010 | Mühlhoff et al. |
| 2004/0102765 A1 | 5/2004 | Koenig |
| 2005/0228366 A1 | 10/2005 | Kessler et al. |
| 2006/0106371 A1 | 5/2006 | Mühlhoff et al. |
| 2007/0010803 A1 | 1/2007 | Bischoff et al. |
| 2007/0179478 A1 | 8/2007 | Dobschal et al. |
| 2007/0237620 A1 | 10/2007 | Mühlhoff et al. |

FOREIGN PATENT DOCUMENTS

| | | |
|---|---|---|
| DE | 10 2004 009 212 A1 | 9/2005 |
| EP | 1 159 986 A2 | 12/2001 |
| WO | WO 03/002008 A1 | 1/2003 |
| WO | WO 2004/032810 A2 | 4/2004 |
| WO | WO 2005/039462 A1 | 5/2005 |
| WO | WO 2005/048895 A1 | 6/2005 | ent is described in EP 1,159,986 A2. It resembles the contact lens of U.S. Pat. No. 6,373,571, but additionally comprises a periphery in the form of a holder having line marks which enable a surgeon to visually position the device. However, such positioning is usually too inaccurate.
APPARATUS AND METHOD FOR MATERIAL PROCESSING USING A TRANSPARENT CONTACT ELEMENT

RELATED APPLICATIONS

This application is a divisional of U.S. patent application Ser. No. 11/864,500, filed Sep. 28, 2007, (U.S. Pat. No. 7,863,543, issuing Jan. 4, 2011), which application claims the benefit of priority to German Patent Application No. 102006046370.6 filed on Sep. 29, 2006. Said applications are herein incorporated by reference herein in their entirety.

FIELD OF THE INVENTION

The invention relates to a material processing apparatus and a method of preparing the material processing apparatus for generating optical breakthroughs on or in an object.

BACKGROUND OF THE INVENTION

The invention relates to a method of preparing an apparatus for material processing by generating optical breakthroughs in or on an object, which apparatus comprises a variable, three-dimensionally acting focus adjustment device for focusing pulsed processing laser radiation on different locations in or on the object, wherein a contact element to be placed on the object is mounted to the apparatus, said contact element being transparent for the treatment laser radiation and comprising, on its side to be placed on the object, a contact surface and, located opposite, an entry surface for the processing laser radiation, each of said surfaces having a previously known shape, wherein, prior to processing the object, the position of the entry surface or contact surface with respect to the focus adjustment device is determined by irradiation of measurement laser radiation on said surface, by focusing measurement laser radiation near or on said surface by means of the variable focus adjustment device, with the energy density of the focused measurement laser radiation being too low to generate an optical breakthrough, and the focus position of the measurement laser radiation is adjusted in a measurement surface intersecting the expected position of said surface.

The invention further relates to a material processing apparatus which comprises a processing laser providing pulsed treatment laser radiation, an optical device for focusing the processing laser radiation into or onto an object to be processed, such that optical breakthroughs form in the focus, a focus adjustment device for variable adjustment of the focus position in or on the object, a contact element to be placed on the object, which contact element can be mounted to the apparatus and comprises a contact surface to be placed on the object and, opposite the contact surface, an entry surface for the treatment laser radiation, each of said surfaces having a previously known shape, and a control device for determining the position of the entry surface or of the contact surface after mounting the contact element and before processing the object, which control device controls the processing laser and the focus adjustment device, there being provided also a measurement laser radiation source, also controlled by the control device, for emission of measurement laser radiation, whose measurement laser radiation passes through the focus adjustment device and the optical device and causes no optical breakthroughs in the focus, wherein the control device, in order to determine the position of the surface, adjusts the focus of the measurement laser radiation in a measurement surface intersecting the expected position of the surface.

In material processing, a laser processing device is often employed to scan the regions of the object which are to be processed by a processing laser beam. The accuracy of positioning the laser beam usually determines the precision achieved in processing. If the laser beam is focused into a processing volume, exact three-dimensional positioning is required. Therefore, for high-precision processing it is usually indispensable to keep the object in an exactly defined position to the laser processing apparatus. For such applications, the aforementioned contact element is used, because it allows fixation of the object to be processed, whereby defined relationships are achievable up to the processing volume. In this way, the contact element becomes part of the beam path of the processing laser radiation.

This is required, in particular, in micro-processing of materials having only low linear optical absorption in the spectral range of the processing laser radiation. For such materials, non-linear interactions between the laser radiation and the material are used in the art, generally in the form of an optical breakthrough being produced in the focus of high-energy laser beams. Since the processing effect then only takes place in the laser beam focus, exact three-dimensional positioning of the focal point is indispensable. Thus, in addition to a two-dimensional deflection of the laser beam, an exact depth adjustment of the focus position is required. The contact element serves to ensure constant optical conditions, which are known with a certain accuracy, in the beam path to the object by mechanically coupling the object and the laser processing device and by also imparting to the object surface a shape having a known optical effect.

A typical application of such a contact glass is the ophthalmic surgery method known as femtosecond LASIK, wherein the laser processing apparatus, provided in the form of a therapeutic instrument, focuses a laser beam into the cornea, forming a focus with dimensions on the order of one micrometer. Then, a plasma forms in the focus, causing a local separation of the corneal tissue. By suitable sequential arrangement of the local separation zones thus generated, microscopic cuts are realized, e.g. a defined partial volume of the cornea is isolated.

The position of the contact element influences the accuracy of this method and, therefore, it is dealt with many times in the literature with respect to position determination:

U.S. Pat. No. 6,373,571 discloses a contact lens provided with reference marks. Said contact lens is adjusted by means of a separate measurement device, resulting in a relatively complex configuration. A further example of a contact element is described in EP 1,159,986 A2. It resembles the contact lens of U.S. Pat. No. 6,373,571, but additionally comprises a periphery in the form of a holder having line marks which enable a surgeon to visually position the device. However, such positioning is usually too inaccurate.

Since the contact element usually contacts the object to be processed, it is generally required to employ a new, separate adapter for each object. This applies, in particular, in ophthalmic applications under the aspect of sterility. As a consequence, prior to each processing operation or prior to surgical intervention, respectively, the contact element has to be mounted to the laser processing device, which is then provided e.g. as a therapeutic instrument. WO 03/002008 A1 teaches to mount the contact glass by holding it in a pincer-like means which is locked to the laser processing device. Said locking is effected via a collar guided within a rail. The adapter is pushed in transversely to the optical axis in a form-locking manner. DE 19831674 A1 describes the use of a mechanical coupling mechanism wherein a metal rod, attached to a mount of a contact glass at an oblique angle, is held in a sleeve by means of a magnet or electro-magnet. However, these attachments do not define the position of the contact element with sufficient accuracy.

It is further known from WO 05/039462 A1 to provide a contact glass with position marks and to add to the laser processing device a confocal detector unit which, in connection with irradiated measurement laser radiation, allows to detect the position of the marks and to determine the position of the contact glass therefrom. The accuracy with which the position of the contact glass is known is thus better than the accuracy given by the mounting mechanism as described in DE 10354025 A1, for example, and by the manufacturing tolerances of the contact glass.

WO 04/032810 A2 also pursues the goal of accurately determining the position of the contact glass. It describes a method or a device of the type described above. For exact determination of the position of the contact surface of the contact glass, which surface is pressed onto the eye, said publication suggests to use the effect of the treatment laser on the contact surface. The treatment laser is controlled such that it is focused at a multiplicity of points and emits treatment laser radiation pulses. Those laser beam pulses which are focused on the boundary surface of the contact glass produce an optical breakthrough by a non-linear effect, which manifests itself as a corresponding plasma spark. Thus, detection of a spark gives an indication that the boundary surface is located at the present focus position of the treatment laser beam. The determination of a sufficient number of such points, which may be arranged in a plane perpendicular to the optical axis of the treatment laser beam, for example, is then used to determine the position of the contact glass. In an alternative approach, said publication suggests to utilize non-linear effects on the contact glass, which are produced by lower energy levels of the treatment laser pulses, i.e. by energy levels causing no optical breakthroughs. Of course, such non-linear effects below the energy threshold for optical breakthroughs occur only with certain contact element materials. The publication mentions non-linear effects in the form of the second harmonic of the irradiated treatment laser radiation or white-light radiation. The measurement or detection of such radiation poses high chromatic demands, because radiation, e.g., of twice the irradiated frequency has to be detected. This makes the optical system complex.

In a third approach, the aforementioned publication suggests to detect the position of the contact surface of the contact glass by means of an interference arrangement. However, the interference patterns produced thereby are generally not suitable for adjustment or consideration by inexperienced users. They are extremely difficult to evaluate automatically. The concept of said citation, as far as it is suitable for application, requires either irradiation of high-energy laser radiation forming optical breakthroughs at the boundary surface of the contact glass, which is disadvantageous under aspects of radiation protection, or requires contact glass materials which exhibit a non-linear effect for the processing laser radiation.

In contact elements, the contact surface to be placed on the object is usually manufactured with great precision. Therefore, the aforementioned methods and devices of WO 04/032810 A2 determine the position of the contact surface, which may be planar, for example.

Therefore, it is an object of the invention to improve a method or device of the above-mentioned type with respect to determining the position of the contact glass.

SUMMARY OF THE INVENTION

According to the invention, this object is achieved by a method of preparing a material processing apparatus, wherein radiation scattered back or reflected back from the focus of the measurement laser radiation is confocally detected, the position of points of intersection between the measurement surface and the entry surface or contact surface is determined by the confocally detected radiation and the assigned setting of the variable focus adjustment device, the above step being repeated several times, if necessary, with a modified, in particular shifted, measurement surface until a determined number of points of intersection, preferably five, have been detected, and the position of said surface is determined from the position of the points of intersection and the previously known shape of the entry or contact surface.

The object is further achieved by an apparatus of the above-mentioned type wherein a confocal detector device is provided which confocally detects radiation scattered back or reflected back from the focus of the measurement laser radiation and supplies measurement signals to the control device, and the control device determines the position of points of intersection between the measurement surface and the entry surface or contact surface, said control device varying, in particular shifting, the measurement surface, if necessary, in case there are no or too few points of intersection, and determining the surface position on the basis of the position of the points of intersection and of the previously known shape of the entry surface or contact surface.

The contact surface is a suitable surface for position determination. If the geometry of the contact element between the entry surface and the contact surface is given with sufficient precision, determination of the position of the entry surface is also conceivable, of course. In particular in the case of planar or spherical contact elements, the geometry between the entry surface and the contact surface can usually be manufactured with such precision that the entry surface position can also be determined for such contact elements. This has the advantage that there is always a clear discontinuity of the refractive index at the usually non-contacted entry surface, regardless of whether the contact element has already been placed on the object.

The invention uses for detection a linear interaction between the measurement radiation and the surface to be detected (i.e. the entry surface or the contact surface). It is neither required to focus laser radiation to an energy density which achieves an optical breakthrough nor does the material of the contact glass have to exhibit a non-linear interaction with the measurement laser radiation below the energy threshold for an optical breakthrough. Also, the optical system of use (e.g. an objective) only has to pick up radiation of the same wavelength as the treatment radiation, which does not give rise to any additional (chromatic) demands. Thus, in contrast to the prior art, the configuration is not made more complex and more expensive by the detection function.

The approach according to the invention serves to determine the exact position of the contact element (also referred to as a contact glass here). Since the boundary surface of the contact glass is usually curved, its shape is commonly described by a coordinate system referring to the contact glass, for example, in the case of a curved contact surface, to a vertex or to any other marked point of the curvature. In contrast thereto, material processing or the apparatus for material processing, respectively, is operated with respect to a coordinate system referring to the apparatus itself. Now, determining the exact position of the contact surface or of the entry surface of the contact glass allows the coordinate system of the contact glass or its surface curvature to be adjusted or adapted to the coordinate system of the apparatus or of the material processing method or to determine and consider the offset existing between the two coordinate systems.

The measurement surface is selected such that it intersects the expected position of the surface to be detected on the contact element. The expected position is previously known because the contact glass is attached to the processing device prior to determining the position. Due to the thus known geometric conditions, the region of the expected position of the surface is predetermined by the tolerances during mounting as well as the possible variations which may result during manufacture of the contact glass or with different types of contact glasses.

By shifting the focus position of the measurement laser radiation in the measurement surface, points of intersection between the measurement surface and the surface to be detected are sought. The confocal detection enables unambiguous detection of the discontinuity of the refractive index which appears at the surface of the contact glass, which is preferably not contacted at this location. If the focus is shifted in the measurement surface, a discontinuity of the refractive index occurs every time the focus is located at a point of intersection between the surface to be detected and the measurement surface, which discontinuity results in a corresponding signal during confocal detection.

The confocal detection of the back-scattered or back-reflected measurement laser radiation advantageously uses the fact that the part of the confocally detected emission radiation which is scattered back at a boundary surface of a transparent medium is significantly higher than within the transparent medium. Due to the spatial filtering occurring in this case, the confocal detection yields a sufficiently strong signal whose strength depends substantially on the difference in refractive index at the contact surface of adjacent media. Thus, for example, said difference is greater for the transition from glass to air than for the transition from glass to lacrimal fluid. Therefore, when determining the position of the contact surface, it is preferred to effect determination of the position before the contact element is placed on the object to be processed, e.g. on the cornea of the eye. Since the energy of the measurement laser radiation does not result in any processing effect, it is also possible, of course, to determine the position of the surface after the contact element has been placed on the object, i.e. has been wetted with lacrimal fluid in the case of ophthalmic surgery.

Of course, the measurement surface need not be completely covered by the focus shift. It is absolutely sufficient if enough points, i.e. a (sufficiently) dense path curve, are located in the measurement surface. The condition to be fulfilled is that a sufficient number of points of intersection for position determination are found. If need be, the number of points in the measurement surface can be increased. Further, any two-dimensional manifold will be sufficient whose extent is such that it intersects the expected position of the known surface to be detected.

Therefore, the focus position is preferably shifted along a path curve located in the measurement surface. The path line should be selected such that it intersects the sought surface of the contact glass, i.e. contains common points between the measurement surface and the surface in the expected position of the latter. It is generally sufficient if the path line yields at least five discernible points of intersection between the measurement surface and the surface to be detected in case of a curved surface to be detected.

Based on the position of the points of intersection, the position of said surface is then determined, taking into consideration the previously known shape of the entry surface or of the contact surface. For non-spherical surfaces, this may also include determining a tilt of the main optical axis of the system.

In the case of a rotationally symmetric surface, fewer points of intersection will be sufficient. For surfaces which are conventionally used for spherically curved contact elements, it is preferred that the measurement surface be located such that it has cylindrical symmetry about the main optical axis of the processing laser beam, preferably the shape of a cylinder shell or of a circular disk. A cylinder is particularly favorable, because it has turned out that the z coordinate, i.e. the coordinate along the main optical axis of the processing laser beam, is subject to particularly great variations with respect to mounting of the contact element and its manufacturing tolerances. Providing the measurement surface as a cylindrical surface has the advantage that a particularly large area can be covered in the z direction (along the main optical axis of the measurement or processing laser radiation). The path line in this cylinder shell can be provided as a spiral, for example. Selecting a sufficient pitch of this spiral will ensure that a sufficient number of points of intersection between the measurement surface and the (rotation symmetric) surface to be detected are given. If necessary, i.e. if there are not enough points of intersection (see above), the path line can be modified in an iterative manner.

Of course, detection of the surface is facilitated by increasing the power of the measurement laser radiation. An optimum signal/noise ratio is achieved at a pulse energy of approximately 20 nJ. The intensity of the measurement laser radiation which can be applied, in particular, in a pulsed manner, is selected such that no optical breakthrough occurs in the focus. Therefore, a pulse energy of less than 300 nJ is preferred for a pulsed measurement laser radiation. This value represents an upper limit which should not be exceeded so as to avoid optical breakthroughs or other non-linear processing effects on the contact element.

Further, the use of as little measurement laser radiation power as possible is recommended so as to keep exposure to radiation as low as possible for users or third parties. Of course, not only the pulse energy, but also the pulse frequency is relevant in this connection, because they both determine the dose together. For a pulse frequency of between 50 and 500 kHz, an upper limit of 10 nJ, or even 5 nJ, is conveniently advantageous, because at typical wavelengths of between 1,000 nm and 1,060 nm, the maximum radiation power which can be focused on the retina by a viewer's eye lens will then remain within a non-hazardous range.

A processing effect on a transparent object can be achieved by an optical breakthrough. However, it is also possible to achieve a processing effect by repeatedly introducing laser radiation pulses into a particular volume element, within a determined, narrow time interval, said pulses being below the threshold for an optical breakthrough. The usual explanation for this effect is that the pulse energy EPULS of the laser radiation can be accumulated in the volume within a comparatively short time and thus leads to a processing effect. In order to avoid this, the number of laser pulses emitted as measurement laser radiation within less than 20 seconds should not exceed a certain number within the maximum extent of said volume. Indicating the maximum extension or length of the path line as D and the pulse frequency as f will yield the following inequation: $f < 20\ Hz * ((D/EPULS)*(1\ \mu J/1\ mm))^4$. The maximum extent D therein is that extent of the path line at which the latter would appear to the observer to be a luminous object, if the observer were able to perceive the spectral range of the measurement laser radiation (with a corresponding spatial resolution). D should be at least 1 µm, but not more than 20 mm. These sizes result from the possible deviations from the expected position of the sought surface.

The aforementioned inequation also takes into account the radiation exposure which the measurement laser radiation should not exceed. Since the maximum extent of the object is applied to the power of four in this inequation, the radiation exposure can be reduced considerably by a suitable selection of the path line, in particular of the lateral extent of the path line.

To provide still further safety for users or other persons, a safety device may also be used during position determination, which safety device absorbs measurement laser radiation possibly transmitted by the contact element. For example, a safety cap can be placed on the contact element, on the side opposite that side where the measurement laser radiation is incident, said safety cap preferably not contacting the contact surface in order to obtain a discontinuity of the refractive index at the contact surface. This is advantageous also for reasons of sterility. As an alternative or in addition, a covering mechanism may be used which is incorporated in the processing apparatus and is activated, e.g. swiveled into position.

Especially in laser surgery, different contact elements are used in many cases, which differ with respect to the geometry of their input and/or contact surfaces. One individualizing parameter may be, for example, the curvature of the surface or the diameter of the contact element. During material processing or during operation of the corresponding apparatus, it should be taken into account, of course, which contact element, i.e. which input or contact surface, is currently present. When determining the position of the surface, the exact shape of said surface is not known. However, what is known is that the shape of the surface belongs to a specific group of shapes, because the supply of possible contact elements is limited, of course. Not least in the case of rotation-symmetric contact elements, but definitely in the case of spherical surfaces, the positions of the surface's vertex and of the surface's edge relative to each other provide an unambiguous indication as to which surface of the limited group of surfaces the contact element currently mounted to the apparatus comprises. Therefore, the position of the vertex of the curved surface is preferably determined, as is the position of the edge of the surface, and the distance or the mutual position of these structures is used to determine which contact element or which contact surface is present. This determination may include determining the radius of curvature.

As already mentioned, the above-mentioned object is also achieved by a corresponding apparatus. Insofar as method steps carried out when preparing such apparatus have been described above or will be described below, such method steps can be carried out, automatically controlled, by a corresponding control device. The intervention of a person effecting treatment is not required. In particular, the method can be carried out fully automatically, by retrieving a corresponding routine in a control program of the apparatus. This applies equally to variants where the object to be processed is not yet in contact with the contact element and also to variants where the contact element has already been placed on the object. Since the measurement laser radiation further has no processing effect (see above), the method according to the invention is not of a therapeutic or diagnostic nature, even if it is employed in connection with ophthalmic surgery.

Of course, the embodiments and features described above or below can also be employed, in an advantageous manner, individually or in other combinations not expressly mentioned.

BRIEF DESCRIPTION OF THE DRAWINGS

The invention will be explained in more detail below, by way of example and with reference to the drawings, wherein.

DETAILED DESCRIPTION

Figure 1:
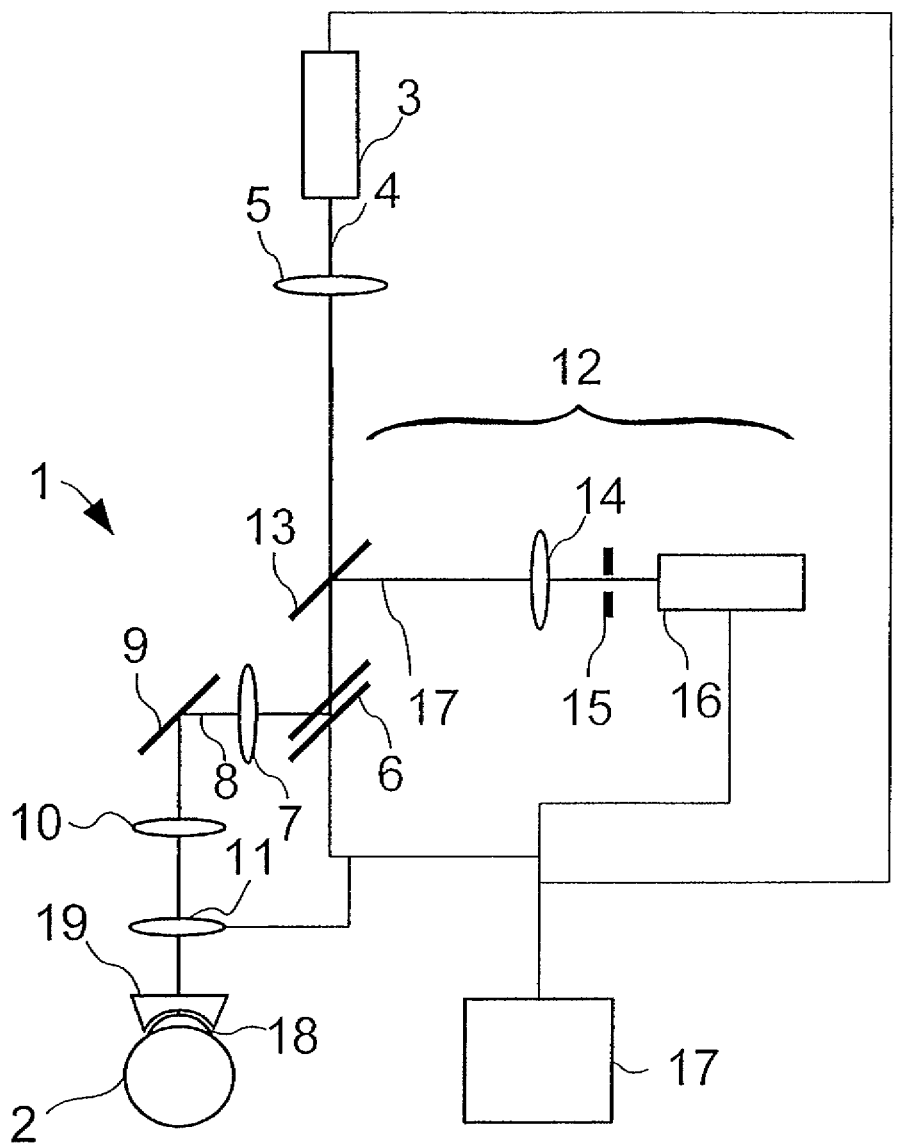
FIG. 1 shows a schematic representation of an apparatus for material processing in the form of a processing apparatus for ophthalmic surgery.

FIG. 1 shows a treatment apparatus for an ophthalmic method similar to those described in EP 1159986 A1 and U.S. Pat. No. 5,549,632. The treatment apparatus 1 serves to carry out a correction of an eyesight defect on the eye 2 of a patient according to the known LASIK method or a similar method. For this purpose, the treatment apparatus 1 comprises a treatment laser 3 which emits pulsed laser radiation. The pulse duration is, for example, in the femtosecond range, and the laser radiation acts by means of non-linear optical effects in the cornea, in the manner described above, e.g. by generating optical breakthroughs in the cornea.

The laser beam 4 emitted by the laser 3 is incident on a scanner 6 which is realized, in the described schematic embodiment, by two scanning mirrors which are rotatable about mutually orthogonal axes. The scanner 6 two-dimensionally deflects the laser beam. Thus, following the scanner 6 as well as its subsequently arranged scanning optics 7, a fan-shaped beam 8 is present, which is adjusted at certain angles with respect to a main optical axis of the direction of incidence, depending on the position of the scanners 6. After deflection by a beam splitter 9, which provides an optical viewfinder for a user, the fan-shaped beam is focused by a tube lens 10 as well as by an adjustable lens 11 to form a focus which is located at the front portion of the eye 2, e.g. the cornea 18. For each ray of the fan-shaped beam, i.e. for each position of the scanner 6, a corresponding lateral displacement of the focus is realized with respect to the main optical axis being present with inactive scanners.

Together with the tube lens 10, the adjustable lens 11 forms projection optics which realize a displacement of the focus along the main optical axis, i.e. in the so-called z direction. Thus, the combination of the lens 11 and the scanner 6 consequently provides a three-dimensionally acting focus adjustment device. This focus adjustment device is controlled by a control device 17 such that, for example, the known LASIK method can be carried out using the apparatus 1.

As already mentioned above, in order to achieve the required constant conditions of incidence on the cornea 18 and in order to subsequently fix them also in space, a contact glass 19, which will be discussed later, is placed on the cornea 18.

The treatment apparatus 1 corresponds to the known construction insofar as it is also described in WO 2004/032810 A2. However, in comparison with the apparatus described therein, the treatment apparatus 1 has a confocal detector 12 added to it. The confocal detector 12 is incorporated in the beam path of the incident laser beam 4 prior to deflection of the latter by the scanner 6. Thus, the beam splitter 13 is located in the resting beam path and has the effect of a color splitter known from laser scanning microscopy, with a non-spectral splitter effect being possible here as well.

The confocal detector 12 detects radiation, i.e. the radiation scattered back or reflected back in the cornea 18, i.e. in the focus selected by the three-dimensionally acting focus adjustment device, and couples it out at the beam splitter 13. The radiation to be detected passes, in the opposite direction, through the beam path of the laser beam 4 from the focus to the beam splitter 13.

Pinhole optics 14 as well as a subsequently arranged pinhole 15 cause the desired confocal filtering with respect to the focus in the cornea 18, so that only radiation scattered back or reflected back from the focus passes to the further subsequently arranged detector 16. The detector 16 is also connected with the control device 17 via lines (not shown), which control device 17 can assign the signal from the detector 16 to the respective focus position by resorting to the corresponding control of the three-dimensional focus adjustment device (scanner 6 and lens 11) and can thus generate an image.

Figure 2:
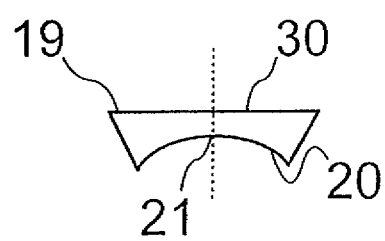
FIG. 2 shows an enlarged schematic representation of a contact glass used in the apparatus of FIG. 1.

The contact glass 19 used in the apparatus 1 of FIG. 1 is shown, schematically enlarged, as a sectional view in FIG. 2. As can be seen, the contact glass 19 has a planar entry surface 30 and a contact surface 20 which is rotation-symmetric in the embodiment example, but is generally planar or curved. As disclosed in WO 2004/032810 A2, planar contact glasses can also be used. Also, the entry surface 30 can be curved. The rotation-symmetric contact glass 19 shown in FIG. 2 comprises a vertex 21 which is defined as the point where the optical axis of the contact glass 19 passes through the contact surface 20 in the case of a rotation-symmetric contact surface 20. Of course, in case of a contact glass 19 having a curved entry surface 30, a vertex (also) exists here. However, by way of example, the construction of FIG. 2 will be assumed in the following.

Figure 3:
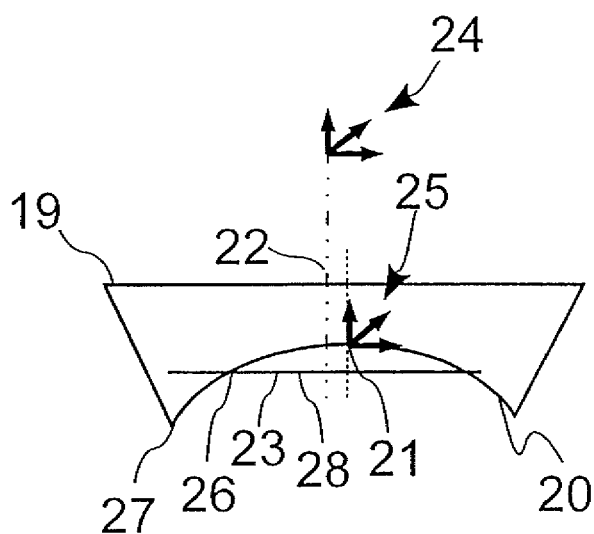
FIG. 3 shows a further enlarged representation of the contact glass of FIG. 2, additionally indicating the position of a measurement surface by means of which the position of the lower side of the contact glass is determined.

As FIG. 3 shows, the curvature of the contact surface 20 is usually described in a coordinate system (for example, by coordinates of a cylinder or of a sphere) relating to the vertex 21. This coordinate system is schematically indicated in FIG. 3 and has the reference numeral 25.

After fixing the contact glass 19 to the treatment apparatus 1, for example by means of a mechanical system as described in WO 05/048895 A1, the contact glass 19 (and thus also its contact surface 20) has a spatial position that is fixed with respect to the treatment apparatus 1, but this position has an inherent tolerance.

Three-dimensional adjustment of the focus is effected in the treatment apparatus 1 in a coordinate system 21 relating to one of the elements of the treatment apparatus 1 which are present during operation, usually the scanner 6 or the contact surface of the contact glass. This coordinate system 24 is schematically indicated in FIG. 3. It usually does not coincide with the coordinate system 25 in which the curvature of the contact glass is described. This is because the main optical axis 22 of the incident laser radiation, due to inevitable tolerances when mounting the contact glass 19 as well as due to the manufacturing tolerances for the contact glass, may usually be shifted and/or tilted with respect to the optical axis or the vertex 21, respectively, of the contact glass 19. There is also usually some uncertainty as to the position of the vertex 21 in the z direction, i.e. in the longitudinal direction of the main optical axis 22, because, in particular, the thickness at the center of a contact glass 19 is very difficult to manufacture within narrow tolerances.

In order to determine the offset between the coordinate systems 24 (of the treatment apparatus 1) and 25 (of the contact glass 19), measurement laser radiation is irradiated through the beam path of the treatment apparatus 1. The treatment laser 3 is then conveniently used as a radiation source for the measurement laser radiation, because, in the embodiment as presented, the treatment laser 3 can be controlled in an operating condition in which it can emit pulsed laser radiation with a pulse energy resulting in no non-linear interaction, in particular no optical breakthrough, in the focus, i.e. after passing through the optical system of the treatment apparatus 1. Suitable attenuators are also possible. Of course, a separate radiation source for measurement laser radiation may also be used. However, it is essential that the measurement laser radiation have a sufficiently precise relationship to the coordinate system 24. This is particularly easy to ensure if the measurement laser radiation also passes through the focus adjustment apparatus, i.e. the scanner 6, the tube lens 10 and the lens 11, i.e. if it is adjusted within the coordinate system 24 of the apparatus. Only then can the offset between both coordinate systems be determined sufficiently exactly.

The measurement laser radiation in the form of a low-energy laser beam 4 is now shifted along a path which is located within a measurement surface 23. The position of the measurement surface 23 is selected such that it intersects the expected position of the contact surface 20. In the embodiment shown in FIG. 3, a measurement surface 23 is selected which, described in cylinder coordinates of the coordinate system 24, is located on a constant z coordinate. Thus, the measurement surface 23 is a surface perpendicular to the main optical axis 22. Accordingly, the coordinates of the curve in the measurement surface 23 of this embodiment differ with respect to their radial coordinates or their angular coordinates, but have a constant z coordinate. The intersection between the measurement surface 23 and the contact surface 20 is a closed path line which is circular in the case of the present spherically curved contact surface 20, because a spherical section which does not contain the center regularly leads to a small circle. Now, this small circle is offset with respect to the main optical axis 22.

This offset is clearly visible in FIG. 4 which shows the view of FIG. 3 from below. The offset as well as the radius of the small circle, which is indicated as the intersecting line 26 in FIG. 4, allows easy calculation of the offset in the coordinate system 25. This applies not only to spherical contact surfaces, but quite generally also to rotation-symmetric contact surfaces, as far as the shape of the contact surface is known. In the case of a spherical contact surface 20, the radial coordinates and the angular coordinates of the center of the small circle on which the points of intersection 26 are located are automatically the corresponding lateral coordinates of the vertex 21. The z coordinate Za results from the z coordinate Zk of the measurement surface 23, as well as the radius of curvature R of the contact surface 3 and the radius r of the aforementioned small circle by the equation: $Za = Zk + R - (R^2 - r^2)^{1/2}$.

Figure 4:
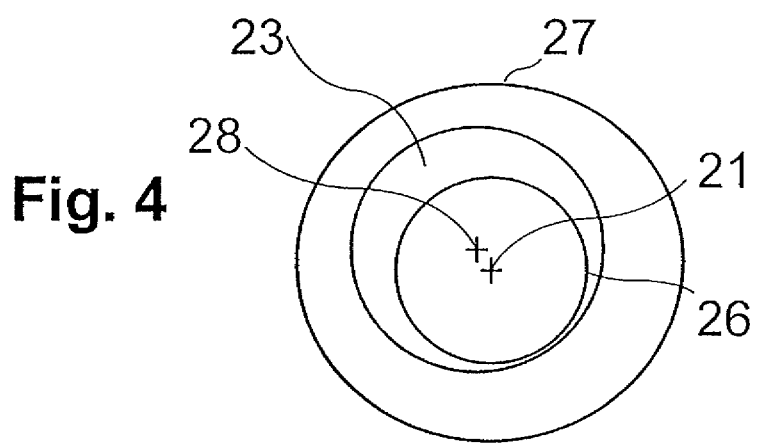
FIG. 4 shows a schematic representation illustrating the position determination, said schematic representation corresponding to a partial bottom view of FIG. 3.

In addition to the aforementioned parameters/structures, FIGS. 3 and 4 also show the edge 27 of the contact surface 20. Said edge 27 can also be detected by suitably shifting the measurement surface 23 along the main optical axis 22. This merely requires the use of a group of measurement surfaces 23 in order to find the edge 27. For example, it is possible, also in the case of a contact surface 20 which is selected from a group of possible contact surfaces, to determine from the radial coordinates of the vertex 21 and the edge 27 that contact surface 20 which is actually present. For this purpose, the person skilled in the art can use the difference in radial coordinates between the vertex 21 and the edge 27. After determining which contact surface of the known group is present, the aforementioned adjustment of the coordinate systems 25 and 24 can then be effected with high precision without having to known in advance which of the contact glasses 19 from a group of possible contact glasses was actually mounted to the apparatus 1.

Figure 5:
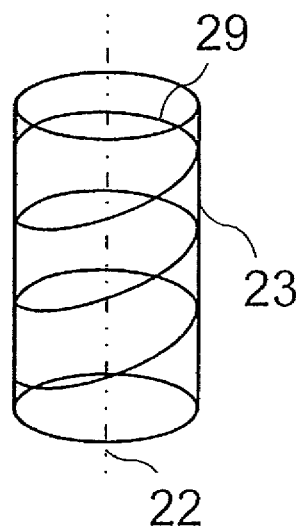
FIG. 5 shows a schematic representation of a further possible measurement surface as well as of a path line located therein, for determining the position of the contact glass in the apparatus of FIG. 1.

FIG. 5 shows a further embodiment, wherein a different measurement surface 23 was used. What applies for all points of the measurement surface 23 here is that the radius is constant in cylinder coordinates of the coordinate system 24. The measurement surface 23 is a cylinder shell. The path line located within this shell can be provided, for example, as a spiral 29. The points of intersection 26 (which are not indicated for the sake of a simpler representation in FIG. 5) which the boundary surface 20 has with the measurement area 23 are in turn located on a closed path line. In this case, it is easy for the person skilled in the art to determine the position of the contact surface 20. In particular, a simple analytical solution can be applied for a spherical contact surface.

The invention claimed is:

1. A method of preparing an apparatus for material processing by producing optical breakthroughs in or on an object, said apparatus comprising a variable three-dimensionally acting focus adjustment device for focusing pulsed processing laser radiation on different locations in or on the object, wherein
   a contact element, which is transparent for the processing laser radiation and is to be placed on the object, is mounted to the apparatus, said contact element having, on its side to be placed on the object, a contact surface and, located opposite, an entry surface for the processing laser radiation, the contact surface having a known shape;
   prior to processing the object, the position of the contact surface with respect to the focus adjustment device is determined by irradiation of laser radiation on the contact surface, by focusing measurement laser radiation near or on the contact surface by the variable focus adjustment device, an energy density of the focused measurement laser radiation being too low to produce an optical breakthrough, and the focus of the measurement laser radiation being adjusted in a measurement surface which intersects the expected position of the contact surface, the method comprising:
   a) confocally detecting radiation scattered back or reflected back from the focus of the measurement laser radiation,
   b) detecting a position of points of intersection between the measurement surface and the contact surface from the confocally detected radiation and the assigned setting of the variable focus adjustment device,
   c) repeating the confocally detecting step, if necessary, with a modified measurement surface until a determined number of points of intersection have been detected,
   d) determining the position of the contact surface from the position of the points of intersection and the previously known shape of the contact surface.

2. The method as claimed in claim 1, wherein the modified measurement surface is modified by shifting it from the measurement surface.

3. The method as claimed in claim 1, wherein the contact surface is non-spherical and the position is determined also with respect to a tilt of the contact surface relative to the optical axis.

4. The method as claimed in claim 1, wherein the focus position is shifted along a path curve which is located in the measurement surface.

5. The method as claimed in claim 1, wherein the measurement surface is cylinder-symmetric to the main optical axis of the processing laser beam.

6. The method as claimed in claim 1, wherein the measurement surface has the shape of a cylinder shell or of a circular disk.

7. The method as claimed in claim 1, wherein the measurement radiation is pulsed with a pulse energy EPULS<300 nJ.

8. The method as claimed in claim 7, wherein the focus position is shifted along a path curve which is located in the measurement surface, has a maximum extent 0 and a pulse frequency f for which $$f < 20\ Hz \ast ((D/EPULS) \ast (1\ \mu J/1\ mm)^4)$$

holds true.

9. The method as claimed in claim 1, wherein a path curve is used which is located in the measurement surface and has a maximum extent 0 of between 1 urn and 15 mm.

10. The method as claimed in claim 1, wherein the measurement laser radiation is provided by a pulsed laser radiation source, which also generates the processing laser radiation, by controlling the radiation source in a mode of reduced pulse energy or by activating or inserting, respectively, an energy attenuator in the beam path of the processing laser radiation.

11. The method as claimed in claim 1, wherein steps a)-d) of claim 1 are carried out after the contact element has been fixed with respect to the focus adjustment device, but before the contact element is placed on the object.

12. The method as claimed claim 1, wherein the contact surface is covered, during irradiation of the measurement laser radiation.

13. The method as claimed in claim 12, wherein the contact surface is covered in a contactless manner.

14. The method as claimed in claim 1, wherein, for a curved surface, the position of a vertex of the surface is determined and is stored as a reference point for the subsequent material processing.

15. The method as claimed in claim 14, wherein the shape of the surface is previously known to belong to a group of several different shapes, each known with respect to its exact geometry, and further comprising determining the position of a surface edge and, based on the relative position of the edge and of a vertex, determining the shape from the group of shapes which the surface has.

16. A material processing apparatus, comprising
   a processing laser which provides pulsed processing laser radiation;
   an optical device for focusing the processing laser radiation in or on an object to be processed such that optical breakthroughs form proximate the focus;
   a focus adjustment device for variable adjustment of the focus position in or on the object,
   a contact element mountable to the apparatus, that is to be placed on the object and which comprises a contact surface to be placed on the object and, opposite the contact surface, an entry surface for the processing laser radiation, the contact surface having a previously known shape;
   a control device for determining the position of the contact surface after mounting of the contact element and before processing of the object, the control device controlling the processing laser and the focus adjustment device;
   a measurement laser radiation source, likewise controlled by the control device, to emit measurement laser radiation, the measurement laser radiation from the radiation source passing through the focus adjustment device and through the optical device and causing no optical breakthroughs in the focus, wherein the control device, to determine the position of the surface, shifts the focus of the measurement laser radiation in a measurement surface intersecting the expected position of the surface;

a confocal detector device which confocally detects radiation scattered back or reflected back from the focus of the measurement laser radiation and supplies measurement signals to the control device, and wherein the control device determines the position of points of intersection between the measurement surface and the surface on the basis of the measurement signals, said control device varying, the measurement surface, if necessary, in case there are no or too few points of intersection, and determining, on the basis of the position of the points of intersection and the previously known shape of the surface, the position of said surface.

17. The apparatus as claimed in claim 16, wherein varying the measurement surface comprises shifting the measurement surface.

18. The apparatus as claimed in claim 16, wherein the control device controls the apparatus for carrying out the method according to claim 1.

19. The apparatus as claimed in claim 16, further comprising a covering mechanism which covers the contact element at the contact surface for absorption of transmitted measurement laser radiation.

20. The apparatus as claimed in claim 16, wherein the measurement laser radiation is pulsed and the pulse energy is between 2 nJ and 300 nJ.

21. The apparatus as claimed in claim 16, wherein the measurement laser radiation source is provided by the processing laser radiation source being controlled in a mode of operation for emission of low-energy laser radiation pulses.

* * * * *

UNITED STATES PATENT AND TRADEMARK OFFICE
CERTIFICATE OF CORRECTION

PATENT NO. : 8,502,113 B2
APPLICATION NO. : 12/983743
DATED : August 6, 2013
INVENTOR(S) : Mark Bischoff et al.

It is certified that error appears in the above-identified patent and that said Letters Patent is hereby corrected as shown below:

In the Claims

Column 12, line 5:

"...radiation is pulsed with a pulse energy $E_{PULS} < 300$ nJ."

should read

--...radiation is pulsed with a pulse energy $E_{PULS} \leq 300$ nJ.--

Signed and Sealed this
Twenty-fourth Day of December, 2013

Margaret A. Focarino
*Commissioner for Patents of the United States Patent and Trademark Office*